United States Patent [19]

Schlager et al.

[11] Patent Number: 4,860,172

[45] Date of Patent: Aug. 22, 1989

[54] LAMP-BASED LASER SIMULATOR

[75] Inventors: Kenneth J. Schlager, Elm Grove; Stephen H. Gorski, Wauwatosa, both of Wis.

[73] Assignee: Biotronics Associates, Inc., Wauwatosa, Wis.

[21] Appl. No.: 145,460

[22] Filed: Jan. 19, 1988

[51] Int. Cl.[4] .............................................. F21V 8/00
[52] U.S. Cl. ...................................... 362/32; 362/253; 178/303.1; 350/96.15
[58] Field of Search .......................... 362/32, 307, 253; 376/6; 128/303.1, 395, 396, 397, 398; 350/96.15, 96.20, 96.1

[56] References Cited

U.S. PATENT DOCUMENTS

| | | | |
|---|---|---|---|
| 2,981,826 | 4/1961 | Mattern | 362/32 |
| 3,327,712 | 6/1967 | Kaufman et al. | 128/398 |
| 3,432,766 | 3/1969 | Morantz | 372/6 |
| 3,516,001 | 6/1970 | Koester et al. | 372/6 |
| 3,779,628 | 12/1973 | Kapron et al. | 350/96.15 |
| 3,930,504 | 1/1976 | De Laforonde | 128/303.1 |
| 4,233,493 | 11/1980 | Nath | 362/32 |
| 4,385,344 | 5/1983 | Gonser | 362/32 |
| 4,411,490 | 10/1983 | Daniel | 362/32 |
| 4,476,519 | 10/1984 | Hayamizu | 362/287 |
| 4,556,875 | 12/1985 | Ishiwatari | 128/303.1 |
| 4,576,435 | 3/1986 | Nishioka | 128/398 |
| 4,616,899 | 10/1986 | Schlafer | 350/96.18 |
| 4,627,068 | 12/1986 | Johnson et al. | 372/6 |
| 4,628,416 | 12/1986 | Dewey | 362/32 |
| 4,681,396 | 7/1987 | Jones | 376/6 |
| 4,729,621 | 3/1988 | Edelman | 350/96.15 |
| 4,807,954 | 2/1989 | Oyamada et al. | 350/96.15 |

Primary Examiner—Ira S. Lazarus
Assistant Examiner—Richard R. Cole
Attorney, Agent, or Firm—Andrus, Sceales, Starke & Sawall

[57] ABSTRACT

Conventional omnidirectional lamp light is converted into a narrowly focused, highly intense beam with a power comparable to certain types of lasers. The lamp light is collected and focused with conventional means into an optical coupling cone which condenses the conventionally-focused beam to a very small diameter for launching into a fiber optic cable. An optical terminator at the end of the optical fiber retains collimation of the beam and a power density comparable to certain types of lasers, such as those used in medical applications.

14 Claims, 1 Drawing Sheet

LAMP-BASED LASER SIMULATOR

BACKGROUND OF THE INVENTION

The present invention relates to an apparatus for producing an intensely bright, highly focused beam of light from a conventional incoherent lamp source. More particularly, the invention is directed, to an apparatus which simulates the brightness, chromatic and focal properties of a laser and is particularly suited for certain medical applications as a substitute for a laser.

Lasers are broadly applied in a wide range of scientific, industrial, military and medical applications. Depending on the application, use is made of one or more of the unique characteristics of laser light, such as its monochromatic and coherence properties, great beam intensity, and the ability to focus on a very small area. For most medical treatment applications, brightness and narrow focus of laser light are the properties of primary interest. In such applications, the highly directional collimated laser beam is most important because the energy can be easily collected and focused with intense brightness in a small area. The narrow collimated beam can also be easily launched into a fiber optic system.

However, lasers are expensive to manufacture and use, and certain types of lasers useful in medical applications cannot be used in fiber optic systems. Nevertheless, lasers are broadly used in many medical applications from general surgery to more specialized uses in cardiology, dermatology, otolaryngology and dentistry.

In surgical applications, the high intensity, narrowly focused beam characteristics may be most important and, in most applications, narrow spectral band-width properties are not important. In other more specialized medical applications of lasers, wavelength band selection is particularly important, and this property of certain types of lasers dictates their choice. For example, a tunable dye laser permits wavelength selection required in certain applications. Thus, notwithstanding their current limitations, lasers do provide a broad adaptability to many medical applications for which no suitable alternative apparatus is available.

Conventional lamp-based lighting systems are, of course, also known and widely used in medical applications. However, because of the inability to generate an intensely bright, highly focused beam with a conventional lamp-based system, such systems have generally been relegated to use for illumination or more limited areas of medical treatment not requiring the intensity and collimation which are characteristic of lasers. Conventional lamp-based systems have also utilized fiber optics to enhance the flexibility of illumination systems or to concentrate and improve the intensity of illumination.

U.S. Pat. No. 4,281,366 discloses a medical examination or surgical lighting apparatus in which reflected tungsten lamp light is focused into a fiber optic bundle for transmission to the site to be illuminated. However, the optical fiber bundle is merely a light transmission medium and provides no increase or enhancement in the power density of the light.

U.S. Pat. No. 4,562,832 discloses a medical illumination apparatus in which conventional lamp light is transmitted through a relatively large diameter monofilament optical guide. The guide is enclosed to enhance its internal reflectivity and light transmission efficiency and to minimize losses. This device is, however, simply a light transmission apparatus concerned primarily with transmitting large amounts of light for illumination.

U.S. Pat. No. 4,385,344 describes the optical fiber transmission of reflected lamp light focused directly into the optical fibers. The reflector concentrated light is first directed through an optical bandpass filter to produce light for the fiber optic transmission in a range suitable for photo curing dental materials. In addition to the control of the wavelength of the transmitted light, relatively large diameter optical fibers are utilized to maximize the amount of light transmitted.

U.S Pat. Nos. 2,981,826 and 4,411,490 disclose tapered light pipes used to concentrate light, either lamp-based or natural, into more narrowly channeled beams. However, neither of the disclosed devices is directed at creating high power density light or to channeling the concentrated light into small diameter fiber optic cables.

SUMMARY OF THE INVENTION

The present invention is directed to an apparatus useful in converting conventional omnidirectional light from lamp-based sources into a narrowly focused highly intense beam similar to certain types of laser beams. Such a lamp-based laser simulator may be substituted for a laser in many medical applications, particularly where a fiber optic cable is used to deliver the power.

The laser simulator system comprises a conventional lamp-based light source mounted in an ellipsoidal reflector which collects the omnidirectional light energy and focuses the light into the entrance face of a light pipe or coupling cone which is tapered to converge in the direction of transmission. A small optical fiber is coupled to the exit face of the coupling cone to receive the concentrated narrow beam and transmit it to the distal end of the optical fiber. An appropriate optical lens system or other optical terminator at the end of the fiber collects the divergent light output and refocusses it to a spot with the required intensity to provide the power necessary for medical applications. Spectral selection of the desired wavelength of light is made with an optical filter.

The coupling cone is used to collect the light and condense it for "launching" into the optical fiber. The cone comprises a high transmittance optical glass rod of frustoconical or other tapered configuration which is covered circumferentially with a material having a low index of refraction to optimize internal reflection of the light within the coupling cone. The concentration of light within the cone increases the power per unit area from the entrance face of the cone to its exit face and, thus, into the optical fiber by approximately the ratio of the entrance to exit face areas.

For a conventional lamp generating an arc image of three millimeters and a coupling cone launching the light into a 2 mm diameter optical fiber, the increase in power is approximately one order of magnitude.

The output from the end of the optical fiber, via a suitable optical terminal such as a collimating and converging lens system, is an intense, narrowly focused high power beam. The beam may be tuned to selected wavelengths through the use of optical bandpass filters placed between the lamp and the cone entrance face and/or through selection of the light source lamp.

DETAILED DESCRIPTION OF THE PREFERRED EMBODIMENT

Figure 1:
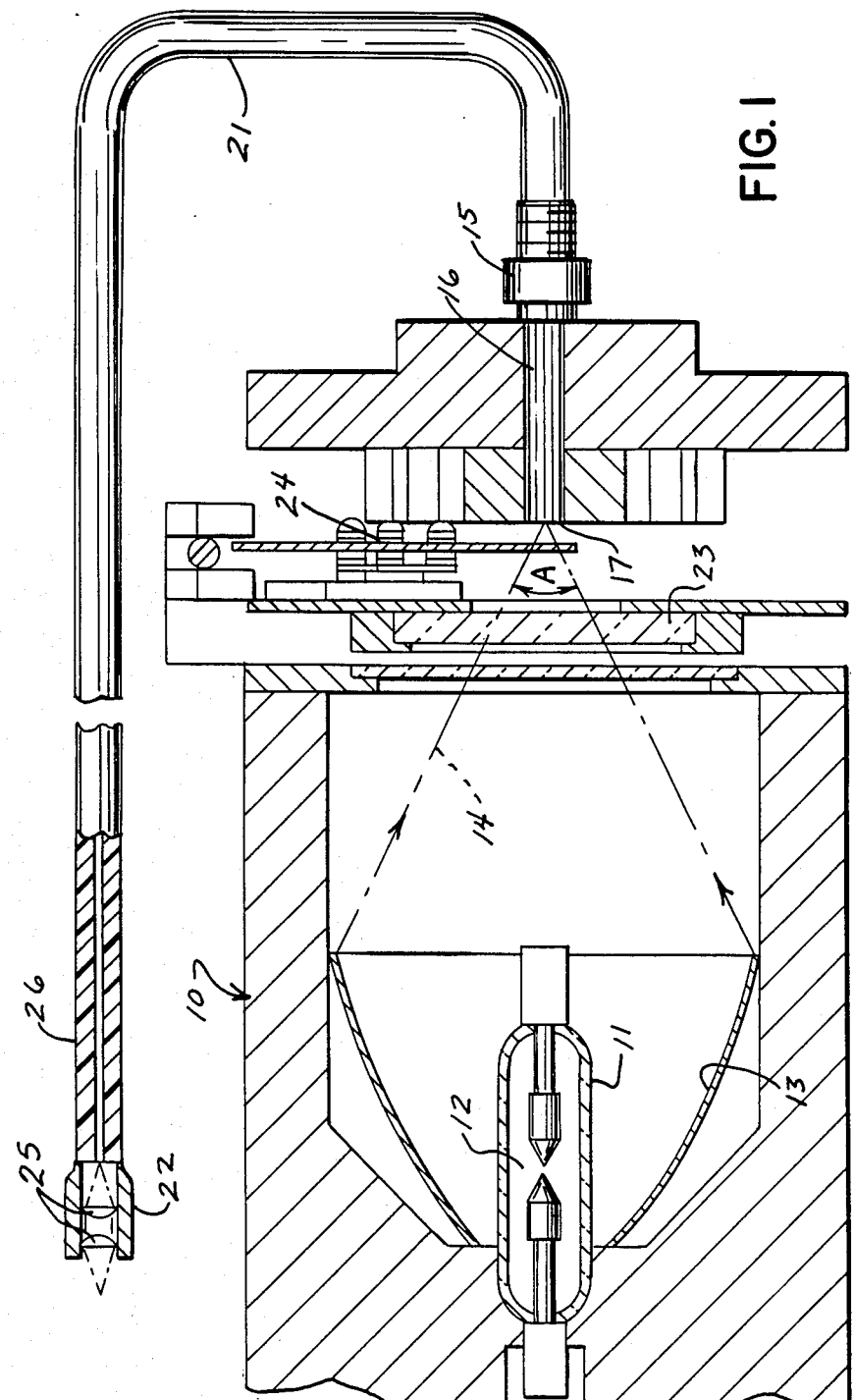
FIG. 1 is a general arrangement of a lamp-based laser simulator of the present invention.
Figure 2:
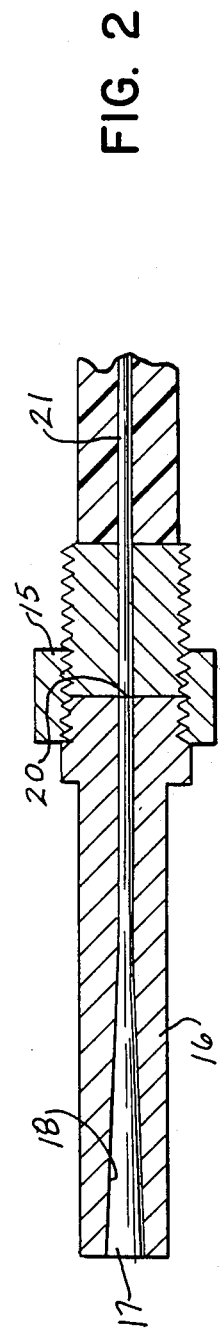
FIG. 2 is an enlarged view of the coupling cone and connection to the fiber optic cable.

Referring to FIG. 1, a lamp-based laser simulator 10 includes a conventional lamp 11 which may comprise an incandescent filament lamp, an arc lamp or a flash lamp. The light producing arc 12 in the arc lamp shown should be relatively small, a size in the range of 0.5 to 3 millimeters generally being suitable. The lamp 11 is positioned within an ellipsoidal reflector 13 which collects the light from the arc or filament source 12 and focuses it onto a distant point. The collection efficiency of the ellipsoidal reflector 13 is about 50%.

The light rays 14 are focused on a distant point at an incidence angle A. A coupling cone 16 is selected and positioned with its planar entrance face 17 at the focal point of the light. The coupling cone is preferably made of high transmittance optical glass with a circumferential cladding 18 of material having a low index of refraction to optimize internal reflection of light within the glass. The cone 16 has a circular cross-section and is tapered to converge in the direction of light transmission and may have a frustoconical shape. However, the taper of the cone may be non-linear as well. The narrow opposite end of the coupling cone 16 terminates in a planar exit face 20 which is parallel to the entrance face 17. The coupling cone 16 functions to collect and condense the light into a narrow, intense beam to be launched into a fiber optic cable 21 coupled to the exit face 20 of the cone.

The fiber optic cable 21 may be coupled to the cone 16 with a number of suitable alternate connections. The choice and manner of making the connection is, however, important because most losses in the system occur as a result of coupling efficiency. As shown in the drawing, the exit face 20 of the cone may be attached in direct abutment to the adjacent face of the cable 21 with a suitable mechanical connector 15. Alternate connections may be made by using an index matching solution or a coupling lens if the adjacent faces are spaced, or fusing the glass components together.

The optical indices of the cone and cladding materials determine the cone acceptance angle which should be equal to or larger than the angle of incidence A of the light. An angle of 30° is typical. Thus, the nature of the focused beam of light should be that it does not exceed the acceptance angle of the cone and does not magnify the source image of the arc 12 significantly.

The gradual taper of the coupling cone 16 is necessary to minimize losses. The light collected and condensed in the cone increases the power per unit area available to be launched into the optical fiber 21 by approximately the ratio of the entrance to exit face areas. Thus, a 3 millimeter arc image from the lamp 11 directed into a coupling cone 16 with an entrance face 17 having a 3 millimeter diameter and an exit face 20 having a 1 millimeter diameter will result in an increase in the light power of approximately one order of magnitude directed into a 1 millimeter diameter optical fiber 21.

The final output of the system 10 must be a focused beam of intense light carried by the small core fiber optic cable. Lamp light collected by the coupling cone 16 and channeled into the optical fiber 21 will exhibit significant divergence as it exits the end of the fiber. The exit divergence is greater than the acceptance angle by a factor proportional to the ratio of the entrance to exit face areas. Collimation is preserved through the use of special beam processing optics at the distal end of the fiber optic cable 21. A typical optical collimator comprises a lens system 22 which reduces light beam divergence and provides the required brightness at the target site. The lens system 22 may comprises a collimating-/converging lens pair 25 which may be conveniently mounted in a wand 26 for directing the output beam to the treatment site.

The present invention allows the simulation of a number of different types of lasers, depending on lamp choice and by the utilization of optical filtering. For example, the tunable dye laser is used in many medical applications requiring wavelength selection in the ultraviolet-visible-near infrared spectral regions. To provide bandwidth selectivity from the broad band light emitted by a lamp 11, an interference bandpass filter 23 may be inserted into the system in front of the coupling cone 16. The filter may conveniently consist of stack of several separate filters, such as a long pass filter and a short pass filter to define the bandwidth and a heat absorbing filter, preferably located nearest the lamp 11, to assist in preventing overheating of the other filters and the fiber optic components. Utilizing a xenon arc lamp of approximately 150 watts and suitable filtering, a dye laser simulator providing therapeutic power of 1 to 2 watts at the fiber optic cable termination can be provided in a 1 mm or smaller diameter core fiber. The power density exceeds that attainable in dye lasers currently in use.

The apparatus may include a shutter 24 disposed in front of the entrance face 17 of the coupling cone to permit selective transmission of light. Transmission may have to be prevented in order to control dosage or to comply with safety restrictions.

$CO_2$ lasers are also widely used in medical applications, particularly in surgical applications requiring a cutting or burning action. One disadvantage of a $CO_2$ laser in such applications, however, is the practical inability to utilize optical fiber transmission of the beam. Not only is the laser itself inherently expensive, but exotic waveguides or beam steering arms must be used with it in typical applications. Simulation of a $CO_2$ laser can be attained through the use of a voltage-derated tungsten lamp with a peak output in the 2.8 to 3.2 micron wavelength band. A monochromatic $CO_2$ laser beam, operating at a wavelength of 10.6 microns, relies on the high absorption coefficient of water for its sharp cutting action. However, the absorption coefficient of water is an order of magnitude greater at a wavelength of 2.6 microns than it is at 10.6 microns. Thus, a lower power $CO_2$ laser simulator can be more effective than a higher power $CO_2$ laser. For example, a 2.5 watt laser simulator would be approximately equivalent to a 25 watt $CO_2$ laser. In addition, the laser simulator utilizes the fiber optic link, making it much more flexible and less costly in its applications.

Both the coupling cone 16 and optical fiber 21 previously described may be of monofilament construction. However, it is also possible to use multifilament bundles of smaller diameter fibers in either the cone or the fiber optic cable. Also, in lieu of the lens pair 25, used as the optical terminator at the end of the fiber optic cable, a graded index rod may be used. A graded index rod can provide the necessary collimation of the light exiting the optical fiber, but its use is somewhat limited at present because of high cost and lower power density rating.

As previously indicated, the lamp light is collected and focused by the ellipsoidal reflector 13 with an efficiency of about 50%. The coupling cone 16 condenses and channels the light into the fiber optic cable 21 with an efficiency of about 40%. The lamp-based laser simulator of the invention described herein, utilizing a fiber optic light delivery system, can provide a light intensity equivalent to a laser. The cost of a laser simulation system is, however, much lower and it is more reliable in operation and is easier to use. In addition, with suitable filtering, the system provides an adjustable wavelength capability.

Various modes of carrying out the invention are contemplated as being within the scope of the following claims particularly pointing out and distinctly claiming the subject matter which is regarded as the invention.

We claim:

1. A laser simulator for generating high energy light beam usuable for medical surgical procedures and the like comprising:
   (a) a lamp-based light source establishing a concentrated light beam of low millimeter dimension;
   (b) a reflector means for collecting and focusing the light;
   (c) a coupling cone for receiving the focused light and concentrating the light into a narrow beam, said coupling cone constructed to maximize energy transfer of the light from the light source;
   (d) an optical fiber coupled to said cone to maximize the energy transfer and receiving the concentrated beam of light from the coupling cone and to transmit the light to its distal end; and,
   (e) optical terminal means at the distal end of the fiber for focusing the light exiting from the fiber wherein said light source generates a ball of light in the range of 0.5 to 3 millimeter and said reflector has an ellipsoidal shape and focuses the light on an entrance end of said coupling cone, said coupling cone having a planar exit face, and said fiber having a planar end abutting the cone exit face for a maximum energy transfer.

2. A laser simulator as defined in claim 1 wherein the coupling cone comprises a body of high transmittance optical glass having a highly reflective internal surface.

3. A laser simulator as defined in claim 2 wherein the coupling cone further comprises:
   (a) an elongated tapered body having a circular cross-section defining an entrance face on the larger diameter end of the body and an exit face on the smaller diameter end of the body; and,
   (b) the ratio of the entrance face to exit face areas being in the range of 3:1 to 10:1.

4. A laser simulator as defined in claim 3 wherein the optical fiber is coupled directly to the exit face of the coupling cone to maximize the energy transfer.

5. A laser simulator as defined in claim 4 wherein the cross-sectional area of the optical fiber is equal to the area of the exit face.

6. A laser simulator as defined in claim 3 wherein the means for collecting and focusing the light comprises an ellipsoidal reflector.

7. A laser simulator as defined in claim 6 wherein the angle of incidence of the light on the entrance face of the coupling cone is not greater than the optical acceptance angle of the cone.

8. A laser simulator as defined in claim 6 wherein the light source comprises a broad band high power lamp.

9. A laser simulator as defined in claim 6 including a bandpass filter disposed between the lens and the entrance face of the coupling cone.

10. A laser simulator as defined in claim 9 wherein the light source comprises a xenon arc lamp.

11. A laser simulator as defined in claim 6 wherein the light source comprises a voltage-derated tungsten lamp.

12. A laser simulator as defined in claim 1 wherein the optical terminal means comprises a collimating and converging lens pair.

13. The simulator of claim 1 wherein said coupling cone is a substantially elongated member having a length which is a substantial multiple of the maximum lateral dimension of the cone.

14. A laser simulator as defined in claim 1 wherein the coupling cone further comprises:
   (a) an elongated tapered body having a circular cross-section defining an entrance face on the larger diameter end of the body and an exit face on the smaller diameter end of the body; said cone having a length which is a substantial multiple of the diameter of the entrance face; and,
   (b) the ratio of the entrance face to exit face areas being in the range of 3:1 to 10:1.

* * * * *